United States Patent [19]

Willert et al.

[11] Patent Number: 5,196,018
[45] Date of Patent: Mar. 23, 1993

[54] KNOCK-OUT INSTRUMENT FOR THE SHANKS OF HIPJOINT PROSTHESES

[75] Inventors: Hans-Georg Willert, Göttingen, Fed. Rep. of Germany; Rudolf Koch, Frauenfeld, Switzerland

[73] Assignee: Sulzer Medizinaltechnik AG, Winterthur, Switzerland

[21] Appl. No.: 879,475

[22] Filed: May 7, 1992

[30] Foreign Application Priority Data

Jun. 26, 1991 [CH] Switzerland .................. 01888/91

[51] Int. Cl.⁵ .............................................. A61F 2/32
[52] U.S. Cl. .................................... 606/99; 606/100
[58] Field of Search ............... 606/90, 99, 100, 82, 606/86, 87, 88; 128/20

[56] References Cited

U.S. PATENT DOCUMENTS

| | | | |
|---|---|---|---|
| 3,801,989 | 4/1974 | McKee | 606/86 |
| 3,818,514 | 6/1974 | Clark | 606/86 |
| 3,857,389 | 12/1974 | Amstutz | 606/86 |
| 3,955,568 | 5/1976 | Neufeld | 606/100 |
| 4,222,382 | 9/1980 | Antonsson | 606/100 |
| 4,459,985 | 7/1984 | McKay | 606/100 |
| 4,642,121 | 2/1987 | Keller | 606/99 |
| 4,927,425 | 5/1990 | Lozier | 606/99 |
| 4,995,875 | 2/1991 | Coes | 606/99 |

FOREIGN PATENT DOCUMENTS 0175079 3/1986 European Pat. Off. .
0244610 3/1987 European Pat. Off. .
2615097 11/1988 France .

*Primary Examiner*—Robert A. Hafer
*Assistant Examiner*—Michael Brown
*Attorney, Agent, or Firm*—Townsend & Townsend

[57] ABSTRACT

The invention shows knock-out instruments for the shanks of hipjoint prostheses, the said instrument consisting of a shank (1) with a coupling-part for a sliding hammer (not shown) as well as of an extension-piece (3) which may be applied in the knock-out direction. The extension-piece (3) is connected rigidly to the shank and stands away from it like a foot at an angle α of between 20° and 60°. The extension-piece exhibits a recess (8) which may be slid from one side over the neck of a hipjoint prosthesis and encircles it over an angle of up to 180°, the width inside the recess measured across the 180° being greater by a clearance than the smallest diameter of the neck of the prosthesis, measured in the same direction. The recess is further formed so that it engages the prosthesis in the area of the neck at three points arranged to lie in a plane substantially parallel to the axis of the shank so that, when the line of action of the sliding hammer is offset relative to the shank axis, a moment generated thereby is opposed by a moment generated between the extension piece and the neck at these three points.

5 Claims, 2 Drawing Sheets

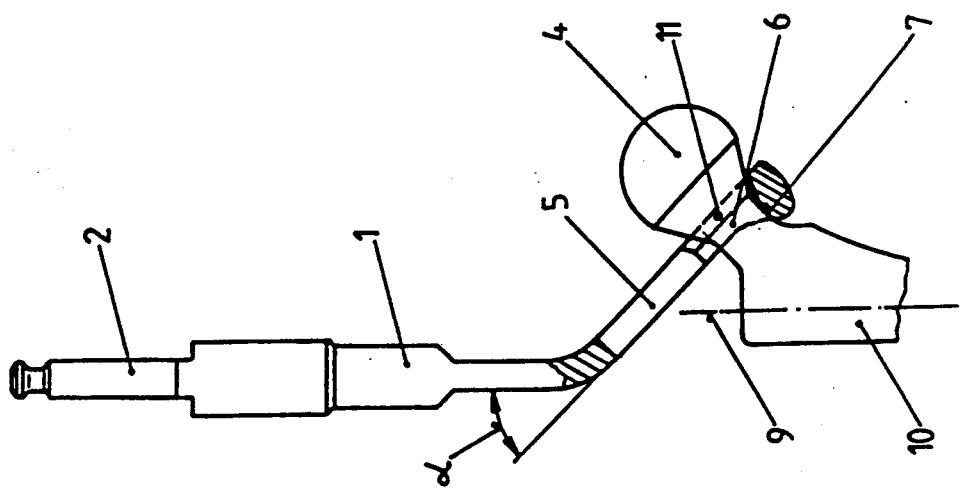
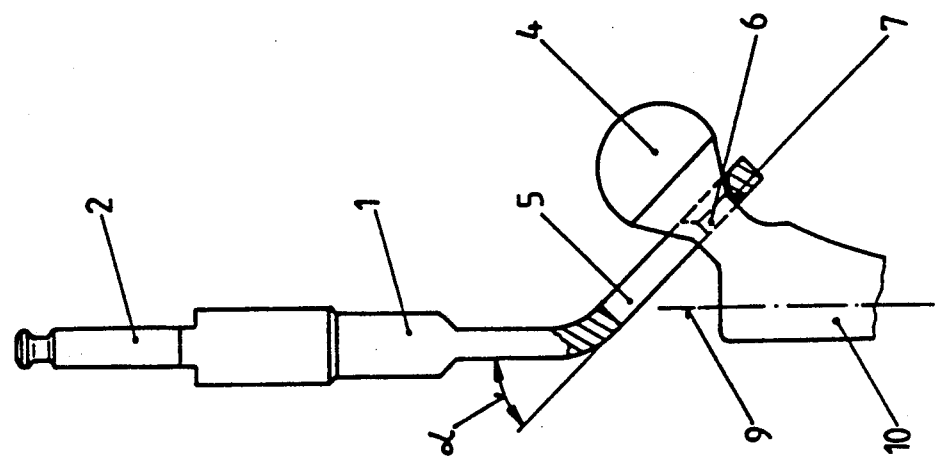
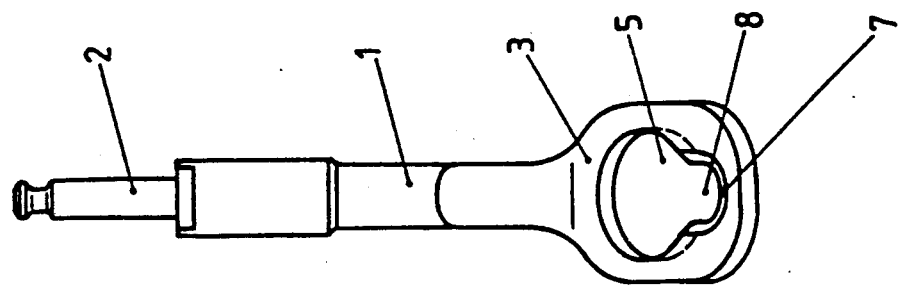

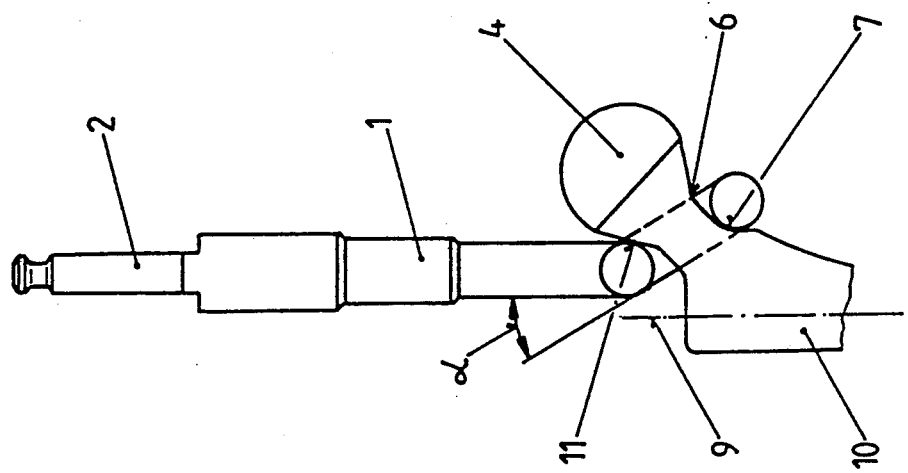
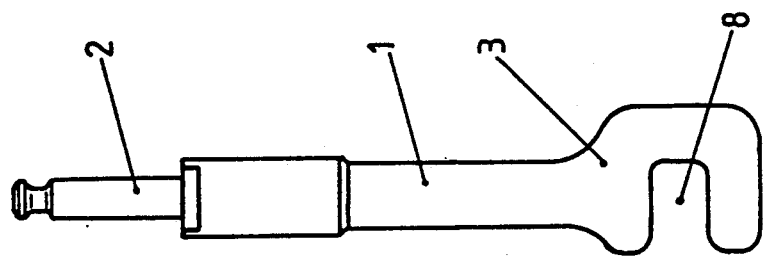

KNOCK-OUT INSTRUMENT FOR THE SHANKS OF HIPJOINT PROSTHESES

BACKGROUND OF THE INVENTION

The invention deals with a knock-out instrument for the shanks of hipjoint prostheses, consisting of a shank with a coupling-part for a sliding hammer as well as of an extension-piece which may be applied in the knock-out direction.

Knocking out the shanks of hipjoint prosthesis is unavoidable in the case of secondary operations in order to prepare the bed in the bone for a new shank. The shanks of prostheses therefore often exhibit holes or tapped holes in the proximal part of the shank of the prosthesis, to which an extractor tool may be applied which is connected via coupling-part to a hammer in such away that the shank is extracted by blows in the direction of extraction because of the inertia of the bone concerned. A knock-out instrument of that kind is shown in the EP 0 244 610. In that case a hook ending as a finger engages in a drilled hole which lies transversely to the axis of the shank of the prosthesis. One disadvantage of the executions hitherto is that holes or possibilities of coupling must be provided on the shank of the prosthesis, which become obstructed by body tissues and depend for their accessibility upon a shank projecting from the prosthesis in the direction of extraction, possibly weaken the prosthesis and in the case of cement-free anchoring reduce the possible area of engagement for a knock-in tool.

SUMMARY OF THE INVENTION

Here the invention creates a remedy. It solves the problem of applying to a femur head prosthesis a rigid one-piece knock-out instrument for the application of which no consideration of any kind is necessary in the construction of the prosthesis.

In accordance with the invention the problem is solved if the extension-piece is connected rigidly to the shank, the extension-piece stands away from the shank like a foot at an angle $\alpha$ of between 20° and 60° and the extension-piece exhibits a recess which may be slid from one side over the neck of the shank of a hipjoint prosthesis and encircles it over an angle of up to 180°, the width inside the recess measured across the 180° being greater by a clearance than the smallest diameter of the neck measured in the same direction.

The advantages of the invention are to be seen in a simple robust extractor tool being available which may be applied to the prosthesis for knocking out without preparatory effect.

BRIEF DESCRIPTION OF THE DRAWINGS

FIG. 1 is a side elevation of an extractor tool in accordance with the invention, which may be introduced over the ball head of the prosthesis;

FIG. 2 is a side elevation turned through 90° with partial sectioning of the arrangement in FIG. 1, which is applied to a prosthesis;

FIG. 3 is an arrangement according to FIG. 2 with a lowest point of contact against the neck of the prosthesis, generated by a bulge;

FIG. 4 is a side elevation of a knock-out tool which may be slid sideways over the neck of the prosthesis; and FIG. 5 is a side elevation turned through 90° of the arrangement in FIG. 4, which is applied to a prosthesis.

DESCRIPTION OF THE PREFERRED EMBODIMENTS

The Figures show knock-out instructions for the shanks of hipjoint prostheses, the said instrument consisting of a shank 1 with a coupling-part 2 for a sliding hammer (not shown) as well as of an extension-piece 3 which may be applied in the knock-out direction. The extension-piece 3 is connected rigidly to the shank and stands away from it like a foot at an angle $\alpha$ of between 20° and 60°. The extension-piece exhibits a recess 8 which may be slid from one side over the neck of a hipjoint prosthesis and encircles it over an angle of up to 180°, the width inside the recess measured across the 180° being greater by a clearance than the smallest diameter of the neck of the prosthesis, measured in the same direction.

In FIGS. 1, 2 and 3 a rigid one-piece knock-out instrument is shown which consists of a shank 1 and a coupling-part 2 continued on the axis of the shank to which a sliding hammer (not shown) may be rigidly coupled.

An extension-piece 3 plane in itself stands away from the axis of the shank at an angle $\alpha$ between 20° and 60° and forms a closed ring with an opening 5 the smallest diameter of which is greater than the diameter of the hipjoint ball 4. At its bottom end the opening 5 is widened by a recess 8 into which the narrowest cross-section of the neck 6 of the prosthesis upon movements in the plane of the extension-piece 3 may still be run straight from medial until the neck 6 of the prosthesis is surrounded over an angle of 180° by the recess 8. A pull in the direction longitudinal to the axis 1 of the shank brings it about so that the recess 8 makes contact at a lowest point 7 and at two points 11 which are offset by 180° and lie towards the ball head at the level of the center of the neck. By creating a bulge as in FIG. 3 the lowest point 7 can adopt a still greater distance from the two contact points 11 in order to clamp the neck of the prosthesis still better in the recess 8 by the two contact points 11 and form a moment of reaction which compensates the moment which arises through the application of force outside the axis 9 of the shank or stem 10 of the prosthesis. If the shank 1 of the knock-out instrument comes in this clamping position to lie on the axis 9 of the stem 10 of the prosthesis a pure tensile load arises via the prosthesis upon the bed in the bone in the direction of the axis 9 of the stem. No additional stresses are superimposed upon the shearing action between the surface of the prosthesis and the bed in the bone, which might impair the strength of the bone.

In FIGS. 4 and 5 the extension-piece 3 again stands away at an angle $\alpha$ between 20° and 60° from the shank 1 of the extractor instrument and a lateral recess 8 accessible from outside is made in it, which may be slid sideways dorsally or ventrally over the narrowest cross-section of the neck of the prosthesis. Upon loading the extractor instrument in tension a moment of reaction is generated on the neck 6 of the prosthesis through clamping between the lowest point 7 and the highest contact point 11, which opposes the torque from the application of force outside the axis 9 of the stem 10 of the prosthesis.

In both embodiments the operating surgeon runs the recess 8 over the neck of the prosthesis and places the extractor instrument under slight tension until through slight tilting of the extractor equipment clamping occurs on the neck 6 of the prosthesis. While preserving the slight prestress which ensures the clamping and rigid connection as regards tensile force, extracting blows are generated by a sliding hammer which has been coupled on, in order to separate the stem V of the prosthesis from its bed in the bone.

What is claimed is:

1. A knock-out instrument for a hipjoint prosthesis, comprising a shank (1) with a coupling-part (2) for a sliding hammer, an extension-piece (3) connected rigidly to the shank (1) and extending away from the shank at an angle α of between 20° and 60°, the extension-piece including a recess (8) formed to be slid from one side over the neck (6) for engaging the neck over an angle of up to 180°, a width measured inside the recess being greater than a smallest diameter of the neck (6) measured in the same direction to provide clearance between them, the extension-piece being shaped to touch the neck (6) at two points (11) offset by 180° and at a lowest point (7), all points (11, 7) lying substantially in one plane which is parallel with the axis (9) of the stem so that a moment generated by the hammer when its line of action is offset with respect to the stem axis is compensated for by a moment generated at said points, whereby the generation of laterally acting forces between the shank and surrounding bone tissue is prevented.

2. A knock-out instrument as in claim 1 wherein the extension-piece includes an opening adjoining the recess (8) and having a diameter which is greater than the diameter of the ball (4) of the hipjoint.

3. A knock-out instrument as in claim 2 wherein the extension-piece includes a bulge and wherein the neck (6) of the shank (10) of the prosthesis enters completely into the recess (8) and touches the extension-piece (3) at the lowest point (7) located at the molded bulge.

4. A knock-out instrument as in claim 1, wherein the recess (8) is oriented transversely to the axis of the shank (1) and wherein the extension-piece is C-shaped so as to provide access to the recess from outside.

5. A knock-out instrument for the removal of an implanted hipjoint prosthesis including a stem embedded in bone, a ball defining an upper end of the prosthesis and a neck connecting the stem with the ball, the ball having a larger diameter than the neck, the instrument comprising a shank for applying hammer blows in an axial direction of the shank, an extension-piece extending at an oblique angle away from one end of the shank and defining a recess shaped to be slipped over the neck by moving the extension-piece transversely to an axis of the neck until it engages the ball so that an axial force applied to the shank is transmitted via the extension-piece to the ball and the stem, whereby hammer blows on the shank generate a force acting in a longitudinal direction of the stem for loosening the stem from the bone, the recess being further shaped to engage the prosthesis at the stem and the ball at first, second and third points, the second and third points being circumferentially spaced apart, the first, second and third points lying on a plane which is substantially parallel to an axis of the stem, and at least one of the points being relatively more distal from the ball than the other points, whereby a moment generated when the axis of the shank is laterally offset from the axis of the stem is compensated by an opposing moment simultaneously generated by forces transmitted from the extension-piece to the prosthesis at the first, second and third points.

* * * * *